United States Patent
Schnarr et al.

(10) Patent No.: US 11,819,290 B2
(45) Date of Patent: *Nov. 21, 2023

(54) DIRECT VISUALIZATION OF A DEVICE LOCATION

(71) Applicant: Medtronic Navigation, Inc., Louisville, CO (US)

(72) Inventors: Alan J. Schnarr, Longmont, CO (US); Marco Capote, Boulder, CO (US); Damon Cook, Louisville, CO (US); Janice Dugger, Westminster, CO (US); Jodi L Kiefer, Broomfield, CO (US); Matthew W. Koenig, Denver, CO (US); Geoffrey M. Ruckel, Denver, CO (US); Jennifer R. Schmasow, Memphis, TN (US); Victor D. Snyder, Erie, CO (US); David Hall, Silverthorne, CO (US); Jacob Gerber, Broomfield, CO (US)

(73) Assignee: Medtronic Navigation, Inc., Louisville, CO (US)

(*) Notice: Subject to any disclaimer, the term of this patent is extended or adjusted under 35 U.S.C. 154(b) by 337 days.

This patent is subject to a terminal disclaimer.

(21) Appl. No.: 17/096,164

(22) Filed: Nov. 12, 2020

(65) Prior Publication Data

US 2021/0059770 A1 Mar. 4, 2021

Related U.S. Application Data

(63) Continuation of application No. 14/695,554, filed on Apr. 24, 2015, now Pat. No. 10,835,322.

(51) Int. Cl.
*A61B 34/20* (2016.01)
*A61B 90/00* (2016.01)
*A61B 34/10* (2016.01)

(52) U.S. Cl.
CPC .............. *A61B 34/20* (2016.02); *A61B 34/10* (2016.02); *A61B 90/37* (2016.02);
(Continued)

(58) Field of Classification Search
CPC ................................................. A61B 34/10–25
See application file for complete search history.

(56) References Cited

U.S. PATENT DOCUMENTS 6,470,207 B1 10/2002 Simon et al.
7,567,834 B2 7/2009 Clayton et al.
(Continued)

FOREIGN PATENT DOCUMENTS

WO 2011-145094 A2 11/2011

OTHER PUBLICATIONS

U.S. Appl. No. 14/695,554, U.S. Pat. No. 10,835,322, filed Apr. 4, 2015, Ruckel, et al.
(Continued)

*Primary Examiner* — Carolyn A Pehlke
(74) *Attorney, Agent, or Firm* — Harness, Dickey & Pierce, P.L.C.

(57) ABSTRACT

A display may display a region of an anatomy that is not within the field of effect of an instrument. The additional views may assist in determining a location and orientation of an instrument. The instrument may be tracked with a tracking system to make the determination of image data to display.

17 Claims, 3 Drawing Sheets

(52) U.S. Cl.
CPC . *A61B 2034/102* (2016.02); *A61B 2034/2051* (2016.02); *A61B 2090/364* (2016.02)

(56) References Cited

U.S. PATENT DOCUMENTS

| | | | |
|---|---|---|---|
| 7,606,613 | B2 | 10/2009 | Simon et al. |
| 7,996,064 | B2 | 8/2011 | Simon et al. |
| 8,105,339 | B2 | 1/2012 | Melkent et al. |
| 8,644,907 | B2 | 2/2014 | Hartmann et al. |
| 10,835,322 | B2 | 11/2020 | Ruckel et al. |
| 2002/0085681 | A1 | 7/2002 | Jensen |
| 2002/0151894 | A1 | 10/2002 | Melkent et al. |
| 2004/0240715 | A1 | 12/2004 | Wicker et al. |
| 2006/0142657 | A1 | 6/2006 | Quaid et al. |
| 2008/0161680 | A1 | 7/2008 | von Jako et al. |
| 2008/0183189 | A1 | 7/2008 | Teichman et al. |
| 2008/0281329 | A1 | 11/2008 | Fitz et al. |
| 2010/0023015 | A1 | 1/2010 | Park |
| 2011/0268248 | A1 | 11/2011 | Simon et al. |
| 2012/0141034 | A1* | 6/2012 | Iannotti ............ A61B 17/1739 382/199 |
| 2014/0323852 | A1 | 10/2014 | Wald et al. |
| 2016/0296285 | A1 | 10/2016 | Chaoui et al. |

OTHER PUBLICATIONS

International Preliminary Report on Patentability dated Nov. 2, 2017 in corresponding International Application No. PCT/US2016/028944.

International Search Report and Written Opinion for PCT/US2016/028944 dated Dec. 9, 2016 claiming benefit of U.S. Appl. No. 14/694,554, filed Apr. 24, 2015.

Invitation to Pay Additional Fees dated Aug. 30, 2016 for PCT/US2016/028944 which claims benefit of U.S. Appl. No. 14/695,554, filed Apr. 24, 2015.

Office Action dated Feb. 4, 2019 in corresponding European Application No. 16724497.9.

Synergy® Spine & Trauma Pocket Guide. Medtronic Navigation, Inc. (Jun. 2, 2014). pp. 1-122.

\* cited by examiner

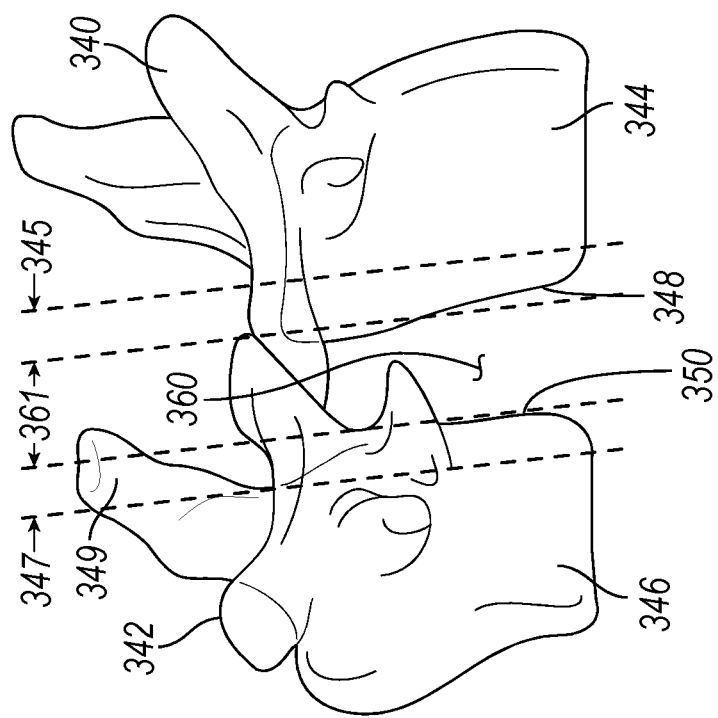
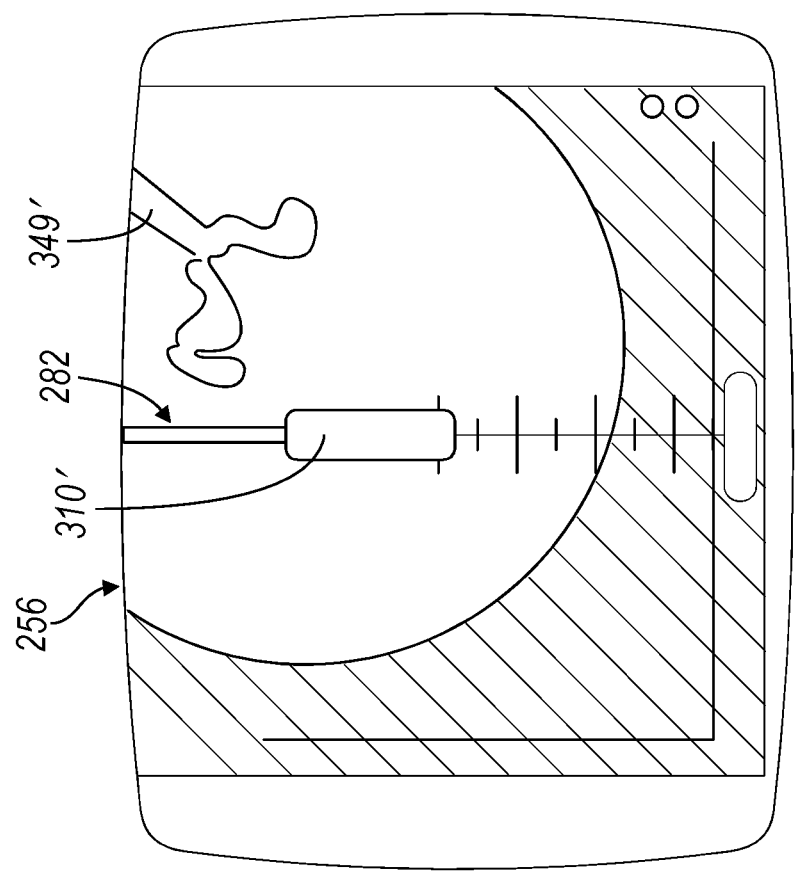
FIG. 2
FIG. 3

DIRECT VISUALIZATION OF A DEVICE LOCATION

CROSS-REFERENCE TO RELATED APPLICATIONS

This application is a continuation of U.S. application Ser. No. 14/695,554 filed on Apr. 24, 2015, now issued as U.S. Pat. No. 10,835,322.

FIELD

The subject disclosure relates to display systems, and particularly to a system for displaying a position of an instrument.

BACKGROUND

This section provides background information related to the present disclosure which is not necessarily prior art.

In a procedure, an instrument can be tracked relative to a portion on which a procedure is performed. According to various systems, the portion having the procedure performed thereon may be a human subject. The procedure may include various surgical procedures, such as a cardiac procedure, neurologic procedure, or spinal procedure, or the like. In specific procedures, an intervertebral body may be replaced. The intervertebral body may include a complete or partial replacement of the intervertebral body (also referred to as a spinal disc) in a spinal column of a patient. To assist in performing the procedure, a location of an instrument may be illustrated with a display device. Image data acquired of a patient, however, may lack detail regarding various anatomical structures, such as soft tissue. Accordingly, the image displayed for viewing by a user may lack details or any information regarding various anatomical structures, such as soft tissues.

SUMMARY

This section provides a general summary of the disclosure, and is not a comprehensive disclosure of its full scope or all of its features.

In a selected procedure, an instrument may be tracked. The procedure may include surgical procedures performed on a subject. The subject may include a living subject, such as a human subject. It is understood, however, that non-human subjects or non-living subjects may also be subject to a procedure. Nevertheless, the location of the instrument may be displayed on a display for viewing by a user to assist in performing the procedure. In various embodiments, the display may illustrate both imaged and non-imaged portions.

A display may display a region of an anatomy that is not within the field of view or directly manipulated or contacted by the surgical instrument. For example, according to various embodiments, an intervertebral implant (also referred to as a disc) trial or implant may be moved relative to a subject. The image data of the subject may include x-ray image data, such as x-ray image slice data, such as computed tomography (CT) slice image data. When illustrating on a display device the image data acquired of a subject, the display may display image data not specifically within the range of the tracked instrument. In various embodiments, therefore, the tracked location of the instruments can be determined and the adjacent anatomical structures may be displayed even though they are not specifically affected by the instrument being tracked. Accordingly, although an intervertebral body instrument or trial is positioned relative to an anatomy, the end plates of vertebral bodies may be displayed when the location of the tracked instrument is determined to be within a predetermined distance range of and adjacent to the vertebral body. Accordingly, a user may better or more efficiently understand and visualize the location of a vertebral body relative to an instrument, which may include an intervertebral body implant or trial for performing a procedure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is a schematic detail view of a two vertebrae;

FIG. 3 is a screenshot of a navigation system illustrating a tracked location of an instrument.

Corresponding reference numerals indicate corresponding parts throughout the several views of the drawings.

DETAILED DESCRIPTION

Example embodiments will now be described more fully with reference to the accompanying drawings.

Figure 1:
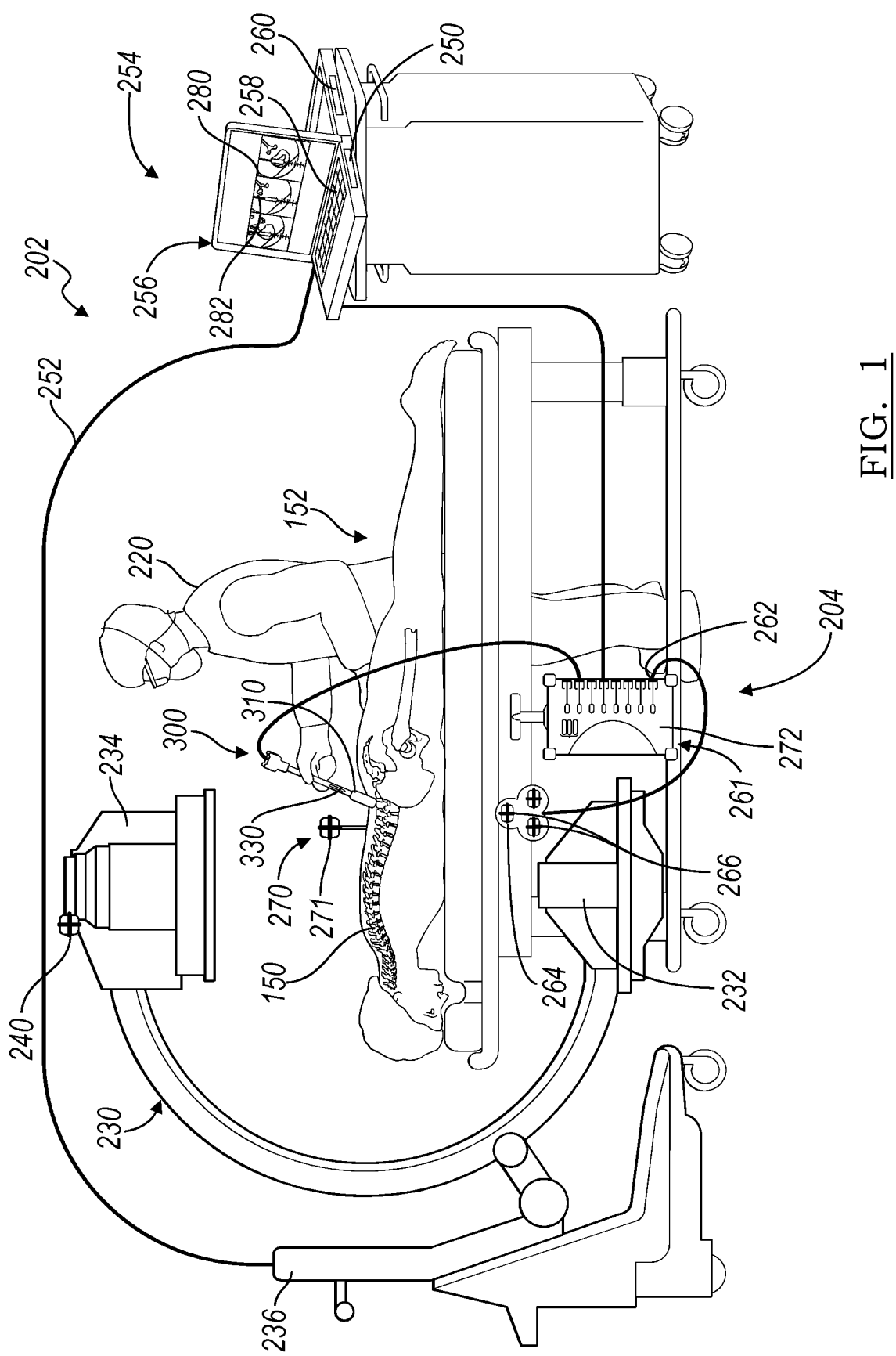
FIG. 1 is a schematic view of a procedure room.

An exemplary electromagnetic (EM) navigation system 202 is shown in FIG. 1. Although the EM navigation system 202 is primarily described with respect to performing a procedure on a human patient 152, the EM navigation system 202 may be used to perform a procedure on other animate and/or inanimate subjects. Also, the implementations disclosed herein may be applied to other EM systems and for purposes other than for position tracking of devices. For example, the implementations may be used to generate EM fields in a transcranial magnetic stimulation system. Also, procedures disclosed herein can be performed relative to a volume, a mechanical device, and/or an enclosed structure. The volume may be of an animate or inanimate object. The subject can be an object that includes an enclosed mechanical device. It is further understood, that any appropriate tracking or navigation system may be used such as an optical tracking system having cameras to track/view viewable portions. Further acoustic/ultrasound tracking systems may be used to track an instrument. Thus, although the disclosure herein relates to an EM navigation system, it is understood that any appropriate navigation system may be used unless specifically indicated otherwise.

With reference to FIG. 1, an instrument assembly 300 may include an appropriate tool or instrument, such as one including a handle or motor and a toolbit or implant portion 310. According to various embodiments, the implant portion 310 may be a trial member for use in trialing an implant placement. The implant may be a trial for an intervertebral or disc replacement. In various procedures, the trial implant 310 may be used to determine or select an appropriate implant size for a specific patient by moving the trial into the implant space.

The instrument 300 may include a portion that is positioned relative to, such as within, a spine 150 of the subject 152. The tool assembly 300 may include a tracking device 330 and may be a navigated instrument. The instrument 300 is merely exemplary, and other navigated instruments may include catheters, leads, stimulators, etc. Also, the tracking device 330 may be incorporated into a separate element, such as a removable stylet. The stylet may be placed within a lumen of a catheter.

The tracking device 330 may be interconnected with the navigation system 202. The navigation system 202, as discussed further herein, may include a tracking system 204 that can track the tracking device 330 in six degrees of freedom, including three-dimensional space including a X, Y, Z location and various orientations to determine a position of the tracking device 330 in space. As illustrated above, the instrument 300 may include the tracking device 330 that allows for directly tracking the tool 300 during an implantation and positioning of tool 300. Appropriate tracking devices can include tracking devices as disclosed in U.S. Pat. No. 8,644,907, incorporated herein by reference. Additionally, the navigation system can include the navigation system disclosed in U.S. Patent Application Publication 2014/0323852, incorporated herein by reference.

With continuing reference to FIG. 1, the tool 300 may be inserted into an opening, such through a surgical opening in a dermal layer of the subject 152 and into an intervertebral space 210 in the spine 150 of the subject 152. The tool 300 may be tracked either directly via the tracking device 330 or via the tracking device on a stylet or other portion associated with the tool 300. Further, as noted above, the tracking device 330 may be associated directly with the trial member 310. Thus, any one or more of these may be used to track the selected portion of the tool assembly 300. Further, the tool 300 may be a catheter that is placed in a vasculature of the subject 152, a nasal cavity, or other portion of the subject 152.

The navigation of the tool assembly 300 relative to the subject 152 may proceed according to various navigation procedures and techniques, such as those generally known in the art and discussed below, to ensure or assist in positioning the trial 310 in a selected, including a predetermined or preselected location, within the subject 152. Further, although the following description is related generally to positioning the tool assembly 300 relative to the spine 150 of the subject 152, other navigated procedures may be performed.

The navigation system 202, which may include an electromagnetic navigation system, is primarily described with respect to performing a procedure on a human patient, the navigation system 202 may be used to perform a procedure on other animate and/or inanimate subjects, including those navigation systems as disclosed in U.S. Pat. App. Pub. No. 2014/0323852, incorporated herein by reference. Also, procedures disclosed herein can be performed relative to a volume, a mechanical device, and/or an enclosed structure. The volume may be of an animate or inanimate object. The subject can be an object that includes an enclosed mechanical device.

The navigation system 202 assists in performing a navigated or guided procedure. The guided procedure can be, for example, a surgical procedure, a vasculature procedure, a cardiac procedure, a neural procedure, a spinal procedure, and an orthopedic procedure. The navigation system 202 allows a user, such as a surgeon 220, to view on a display 256 a position of the tool assembly 300 in a coordinate system. The coordinate system can be related to an image, such as in an image guided procedure, or can be related to an imageless procedure.

The navigation system 202 can operate as an image-based system or as an imageless system. While operating as an imageless system, the navigation system 202 can register a subject space (generally defined within and near the subject 152) to a graphical display representing an area of the subject 152, rather than to both the subject space and an image space. Image data of the subject 152 need not be acquired at any time, although image data can be acquired to confirm various locations of instruments or anatomical portions of the subject 152. Positions of the subject 152 can be tracked and positions of the tool assembly 300 relative to the subject 152 can be tracked.

While operating as an imageless system, a position of an anatomical structure can be determined relative to the instrument and the positions of the anatomical structure and the instrument can be tracked. For example, a plane of an acetabulum can be determined by touching several points with the tool assembly 300, or selected tracked tool with at least one of the tracking devices 330. As another example, a position of a one or more vertebrae may be determined in a similar manner or by attached one or more dynamic reference frames (DRF) 270 to selected vertebrae. The position of the tool assembly 300 and the anatomical structure can be shown on a display with icons or graphics. The display, however, may not show actual image data captured of the subject 152. Other data can be provided, such as atlas data or morphed atlas data. The atlas data can be image data that is generated or generalized from the subject 152. For example, a brain atlas can be generated based on detail analysis of image data of a brain of a patient. Operation of the navigation system 202 as an image based system is further described below.

Although the navigation system 202 is described herein as acquiring image data using an imaging device 230, other data may be acquired and/or used, such as patient and non-patient specific data. The imaging device 230 acquires pre-, intra-, or post-operative image data and/or real-time image data of a subject 152. The imaging device 230 can be, for example, a fluoroscopic x-ray imaging device that may be configured as a C-arm having an x-ray source 232 and an x-ray receiving device 234. Other imaging devices may be included and mounted on the imaging device 230. Calibration and tracking targets and radiation sensors may be included with the imaging system 230.

The navigation system 202 may further include an imaging device controller 236. The imaging device controller 236 controls the imaging device 230 to (i) capture x-ray images received at the x-ray receiving section 234, and (ii) store the x-ray images. The imaging device controller 236 may be separate from the imaging device 230 and/or control the rotation of the imaging device 230. For example, the imaging device 230 can move in selected directions around the patient 152. Also, the imaging device may include an O-arm® imaging device as sold by Medtronic, Inc., having a place of business in Minnesota.

Further, an imager tracking device 240 may be included to track a position of selected portions of the imaging device 230 to identify the position of the imaging device 230 relative to the subject 152 while acquiring the image data to assist in registration. The image data can then be forwarded from the imaging device controller 236 to a processing module of a navigation computer 250 wirelessly or via a link 252. The navigation computer 250 can include a processing module that is configured to execute instructions to perform a procedure.

A work station 254 can include the navigation computer 250, a navigation display 256, a user interface 258, and an accessible memory system 260. The image data may be transmitted from the controller 236 to the work station 254 or to a tracking system 204. The workstation 254 may be a portable computer, such as a laptop computer or a tablet computer. The navigation computer 250 including the computer module may include a general purpose processor that executes instructions for navigating the tool assembly 300 and/or may include an application specific circuit. The tracking system 204, as discussed further herein, may include a coil array controller (CAC) 261 having a navigation device interface (NDI) 262.

While the imaging device 230 is shown in FIG. 1, any other alternative 2D, 3D or 3D imaging acquired over time to include four dimensions, imaging modality may also be used. Examples include those discussed above, and further any imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), intra-operative, computed tomography (CT), single photo emission computed tomography (SPECT), and/or planar gamma scintigraphy (PGS) imaging devices may be used. Any of these imaging devices may be used to acquire pre- or post-operative and/or real-time images or image data of the subject 152. The images may also be obtained and displayed, generally, in two or three dimensions. In more advanced forms, 3D surface rendering regions are achieved of the subject, which may be rendered or changed in time (fourth dimension). The 3D surface rendering regions may be achieved by incorporating subject data or other data from an atlas or anatomical model map or from pre-operative image data captured by MRI, CT, or echocardiography modalities. Image data sets from hybrid modalities, such as positron emission tomography (PET) combined with CT, or single photon emission computer tomography (SPECT) combined with CT, can also provide functional image data superimposed onto anatomical data to be used to reach target sites within the subject 152.

The navigation system 202 further includes the tracking system 204. The tracking system 204 includes a localizer 264, which may also be referred to as a transmit coil array (TCA), a tracking array, or a transmit coil assembly. As noted above, the tracking system may include a non-EM tracking system, thus the localizer may be a camera array, an acoustic array, etc. as generally known in the art. The TCA 264 includes one or more coil groups or sets 266, as discussed further herein, that can transmit or receive a signal and/or generate a field. The tracking system 204 may include the CAC 261, the localizer 264, and the instrument tracking device 330 of the tool assembly 300. It is understood that the tracked portion may be generally referred to as an instrument and that the tracking device may be generally referred to as an instrument tracking device. The tracking system may also track a dynamic reference frame (DRF) 270. All tracked portions are connected to the CAC 261 via the NDI 262. The CAC 261 and the NDI 262 can be provided in a CAC/NDI container 272. The NDI 262 may have communication ports that communicate with the localizer 264, the instrument tracking device 330 and/or the DRF 270 wirelessly or via wires.

The coil arrays localizer 264 can transmit signals that are received by the DRF 270 and at least one tracking device 271 (e.g., the instrument tracking device 330). The tracking device 330 can be associated with the tool assembly 300 at a location that is generally positioned within the subject 152 during a procedure. The DRF 270 can then transmit and/or provide signals, from the DRF tracking device 271, based upon the received/sensed signals of the generated fields from the localizer 264 and/or other localizers. It is understood that the tracking system may also be operated in reverse, where the tracking devices 330 271 transmit a field that is sensed by the TCA 264.

The DRF 270 can be connected to the NDI 262 to forward the information to the CAC 261 and/or the navigation computer 250. The DRF 270 may be fixed to the subject 152 and adjacent to the region where navigation is occurring such that any movement of the subject 152 is detected as relative motion between the localizer 264 and the DRF 270. The DRF 270 can be interconnected with the subject 152. Any relative motion is indicated to the CAC 261, which updates registration correlation and maintains accurate navigation.

In operation, the navigation system 202 creates a map between points in image data or an image space, such as one defined by an image 280 shown on the display 256, and corresponding points in a subject space (e.g., points in an anatomy of a patient or in a patient space). After the map is created, the image space and subject space are registered to each other. This includes correlating position (location and orientations) in an image space with corresponding positions in a subject space (or real space). Based on the registration, the navigation system 202 may illustrate an icon 282 (which may include a three-dimensional rendering of the instrument, including the tool assembly 300) at a navigated position of the tool assembly 300 relative to an image of the subject 152 in a super-imposed image. For example, the icon 282 can be illustrated relative to a proposed trajectory and/or a determined anatomical target. The work station 254 alone and/or in combination with the CAC 261 and/or the C-arm controller (or control module) 236 can identify the corresponding point on the pre-acquired image or atlas model relative to the tracked tool assembly 300; and display the position on display 256 and relative to the image 280. This identification is known as navigation or localization. The work station 254, the CAC 261, and the C-arm controller 236 and/or selected portions thereof can be incorporated into a single system or implemented as a single processor or control module.

To register the subject 152 to the image 280, the user 220 may use point registration by selecting and storing particular points from the pre-acquired images and then touching the corresponding points on the subject 152 with a pointer probe or any appropriate tracked device. The navigation system 202 analyzes the relationship between the two sets of points that are selected and computes a match, which allows for a correlation of every point in the image data or image space with its corresponding point on the subject 152 or the subject space.

The points that are selected to perform registration or form a map are the fiducial markers, such as anatomical or artificial landmarks. Again, the fiducial markers are identifiable on the images and identifiable and accessible on the subject 152. The fiducial markers can be artificial landmarks that are positioned on the subject 152 or anatomical landmarks that can be easily identified in the image data.

The navigation system 202 may also perform registration using anatomic surface information or path information (referred to as auto-registration). The navigation system 202 may also perform 2D to 3D registration by utilizing the acquired 2D images to register 3D volume images by use of contour algorithms, point algorithms or density comparison algorithms.

In order to maintain registration accuracy, the navigation system 202 tracks the position of the subject 152 during registration and navigation with the DRF 270. This is because the subject 152, DRF 270, and localizer 264 may all move during the procedure. Alternatively the subject 152 may be held immobile once the registration has occurred, such as with a head holder. Therefore, if the navigation system 202 does not track the position of the subject 152 or an area of an anatomy of the subject 152, any subject movement after registration would result in inaccurate navigation within the corresponding image. The DRF 270 allows the tracking system 204 to track the anatomy and can be used during registration. Because the DRF 270 is rigidly fixed to the subject 152, any movement of the anatomy or the localizer 264 is detected as the relative motion between the localizer 264 and the DRF 270. This relative motion is communicated to the CAC 261 and/or the processor 250, via the NDI 262, which updates the registration correlation to thereby maintain accurate navigation.

The tracking system 204 can position the localizer 264 adjacent to the patient space to generate an EM field (referred to as a navigation field). Because points in the navigation field or patient space is associated with a unique field strength and direction, the tracking system 204 can determine the position (which can include location and orientation) of the tool assembly 300 by measuring the field strength and direction or components of the EM field at the tracking device 330. The DRF 270 is fixed to the subject 152 to identify the location of the subject 152 in the navigation field. The tracking system 204 continuously determines the relative position of the DRF 270 and the tool assembly 300 during localization and relates this spatial information to subject registration data. This enables image guidance of the tool assembly 300 within and/or relative to the subject 152.

To obtain a maximum accuracy it can be selected to fix the DRF 270 in each of at least six degrees of freedom. Thus, the DRF 270 or any tracking device, such as the tracking device 330, can be fixed relative to axial motion X, translational motion Y, rotational motion Z, yaw, pitch, and roll relative to a portion of the subject 152 to which the DRF 270 is attached. Any appropriate coordinate system can be used to describe the various degrees of freedom. Fixing the DRF 270 relative to the subject 152 in this manner can assist in maintaining maximum accuracy of the navigation system 202.

The tool assembly 300 can include the stylet, drill, etc., as discussed above. Thus, reference to the tool assembly 300 is not intended to limit the instrument that may be tracked and navigated. With reference to any appropriate navigated instrument, it may include the tracking device 330 that may include a power source and/or be connected directly to the CAC 261.

In the navigation system 202, illustrated in FIG. 1, the spine 150 may be the object of a procedure. During the procedure, the image data acquired of the spine 152 may be displayed on the display device 256. In displaying the image of the spine, however, generally, the portion of the spine being directly affected by the instrument 300 is displayed on the display device 256. Accordingly, certain parts of an anatomy may not be viewable with a limited display.

With continued reference to FIG. 1 and additional reference to FIG. 2, image data can be acquired of the spine 150 prior to a procedure. The image data may be acquired with the imaging system 230, or any appropriate imaging system. Further examples include the O-arm® imaging device or a CT imaging system.

Image data regarding the spine 150 can be displayed on the display device 256 relative to the icon 282 of the instrument 300, including the trial 310 as trial icon 310'. This can allow the surgeon 220 to visualize on the display 256 the determined location of the trial 310 relative to the spine 150. As is understood in the art, however, image data acquired of the subject 152, including the spine 150, can be acquired in various manners, including those discussed above. In various examples, slice image data can be acquired of the spine 150, such as with a CT imaging device. Such image data generally includes slices that are taken axially along the length of the spine 150. As illustrated in FIG. 2, the spine 150 can include adjacent vertebrae 340 and 342. The vertebrae 340, 342 can include various anatomical portions including vertebral bodies 344 and 346. Each of the vertebral bodies can include end plates. For example, the vertebral body 344 may include an superior end plate 348 and the vertebral body 346 may include an inferior end plate 350. Further, the vertebrae may each include a spinous process, such as spinous process 349.

It is understood that each of the vertebral bodies 344, 346 may both include inferior and superior endplates, but generally, the inferior endplate 350 and the superior endplate 348 are adjacent to or contact a disc or define a disc or intervertebral body space 360. In various embodiments, the intervertebral implant 310 can be positioned in the intervertebral space 360 when the natural intervertebral body is damaged or degenerated. Various implants and trials can include the implants and system portions included with the Prestige® Cervical Disc or the Bryan® Cervical Disc System, both sold by Medtronic, Inc., having a place of business in Minnesota. Further, it is understood that discs may be replaced in other portions of the anatomy, including lumbar and thoracic regions of the spine 150.

During imaging of the spine 150, the disc space 360 can be imaged along with portions of the adjacent vertebrae 340, 342. As is understood in the art, however, CT image slices may generally be substantially thin, such as on the order of one or a few millimeters thick. Additionally, CT or other x-ray imaging techniques may not image soft tissue with high contrast. Further, certain imaging techniques may allow for imaging portions of the anatomy, such as the intervertebral space 360, while not imaging the adjacent vertebral bodies 344, 346. Alternatively, or in addition thereto, as discussed further herein, during navigation of the trial or the implant 310, the display 256 may display generally the intervertebral space 360 as this is where the implant portion 310 is positioned. Thus, if the imaging technique does not acquire image data of the soft tissue, the display may be substantially free to anatomical portions, as illustrated in FIG. 3.

Accordingly, with additional reference to FIG. 3, in various embodiments, the display 256 may generally include substantially only the icons 282, 310' representing the instrument 300 and/or the implant member 310. It is understood that although the following discussion may refer to the implant or trial 310, that the portion 310 may refer to either or both an implant and a trial, or other appropriate portion, being navigated relative to the patient 152. Nevertheless, the icon 282 may generally be the only displayed portion on the display device 256 as the imaging technique acquiring image data of the spine 150 may not substantially image soft tissue, such as a disc or portion of a disc in the disc space 360.

As the display 256 is displaying the anatomy adjacent to or at the dimensions of the tracked implant 310, adjacent portions of the vertebrae 340, 342 may not be illustrated, such as the endplates 348, 350. As illustrated in FIG. 3, the implant portion 310 may include a surface that is illustrated in the icon 310' and only image portions that are in the same plane are shown. Thus, the disk space 360 includes no high contrast tissue (e.g. bone). However, portions of the bone, such as the spinous process 349 may extend into the plane (although not within the disk space 360) and may be seen in the view as spinous process portion 349'. In various embodiments, therefore, a precise relative position of the implant 310 to the endplates 348, 350 may not be known as visual clues may be missing regarding the endplates 348, 350. For example, the surgeon 220 may not have direct visualization on the display device 256 of the spacing of the implant 310 relative to the endplates 348, 350.

Figure 4:
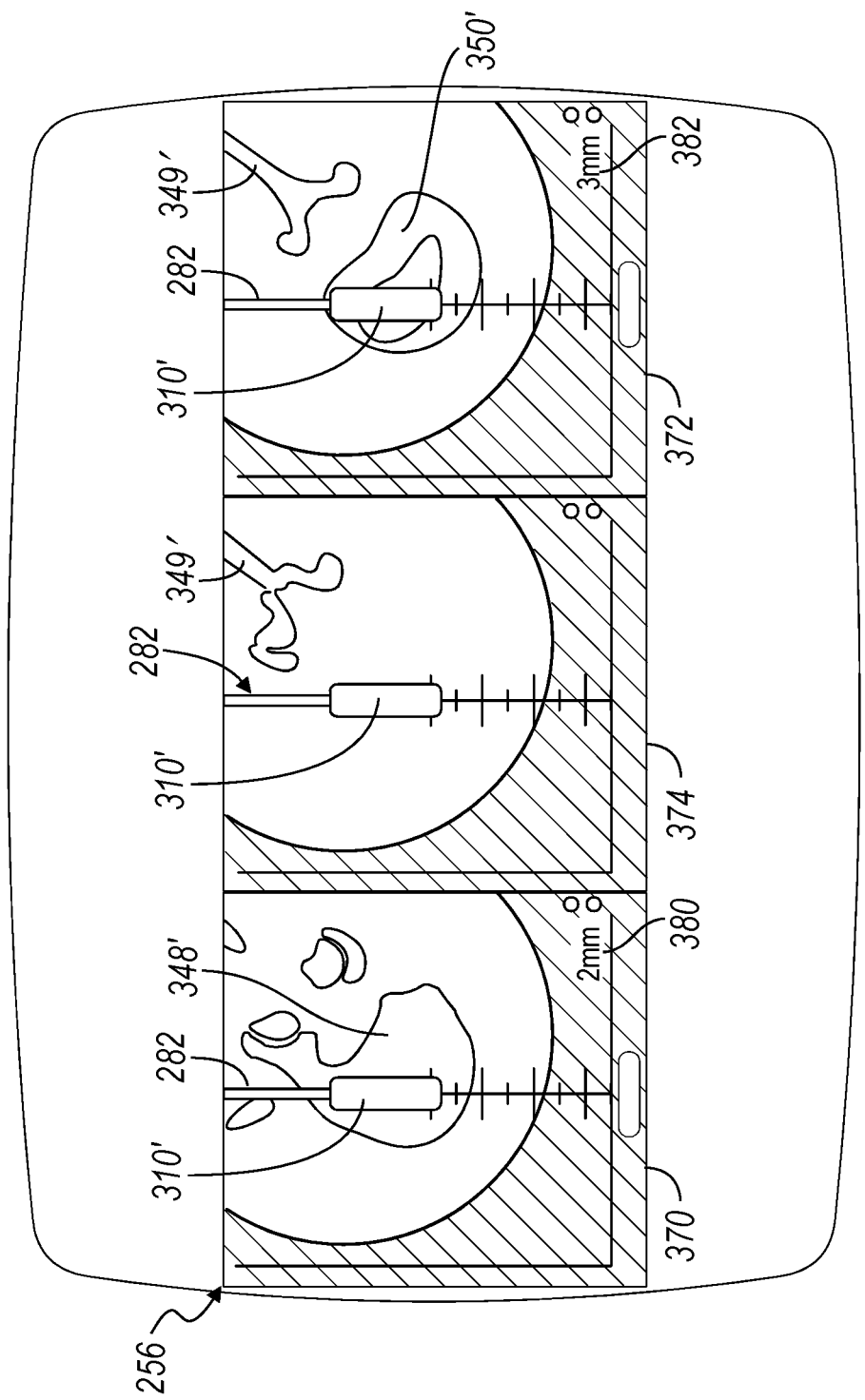
FIG. 4 is a screenshot of a navigation system showing three views of a tracked location of an instrument.

With reference to FIG. 4, the display 256 may be altered based upon instructions from the user 220, direction from the user 220, or substantially automatically by the navigation system 202. As discussed above, the tracking device 330 is tracked relative to the subject 152, including the spine 150. Due to the registration of the subject space to the image space, the navigation system 202 can determine, by tracking the tracking device 330, the position of the implant 310 relative to the spine 150, including the intervertebral space 360. Accordingly, once the navigation system 202 has determined that the implant 310 is in or near the intervertebral space 360, the navigation system can alter the display 256 to include further images based upon image data of the subject 152. As illustrated in FIG. 3, limiting the display 256 to display only the icon 282 may limit the amount of visual cues for the user 220 regarding the position of the implant 310 relative to the endplates 348, 350. Moreover, the navigation processor is configured to scale the displayed representation of the instrument, such as the implant, relative to either of the first image or the second image.

With reference to FIG. 4, however, a first screen portion 370 may illustrate the inferior endplate 348 as an image portion 348' and a second screen portion 372 may illustrate the superior endplate 350 as an image portion 350'. Additionally, a third screen portion 374 may illustrate the intervertebral space 360 substantially alone with the icon 282 of the instrument including an intervertebral implant portion 310'. As discussed further herein, therefore, the display 256 may display an icon representing the implant 310 and portions of the vertebrae 340, 342.

With continued reference to FIG. 4, the display 256 may automatically or manually, or combinations thereof, display the three screen portions 370-374 to provide visual guidance and cues to the user 220. For example, the user may view the screen portions 370-374 to view differing perspectives of the implant 310 relative to the anatomy. All of the view portions 370-374 may be shown on a single display device or screen 256, as illustrated in FIGS. 1 and 4. For example, the first screen portion illustrates the icon 310' superimposed on the superior endplate of the vertebral body 344. Thus, the screen portion 370 may provide an inferior-to-superior viewing perspective. The second screen portion 372 illustrates the icon 310' superimposed on the inferior endplate of the vertebral body 346. Thus, the screen portion 372 may provide a superior-to-inferior viewing perspective. The perspectives may be labeled on the screen portions 370 and 372 for identification by the user 220.

Further, the user 220 may view the display screen portions 370-374 to understand dimensions of the implant 310, represented by the icon 310' relative to the endplate images 348', 350'. For example, as illustrated in the screen portion 370, the user 220 can view the implant icon 310' relative to the medial-to-lateral and posterior-to-interior dimensions of the vertebrae endplate 348 based upon the image portion 348'. Further, a height dimension may be illustrated or written on the display, such as in a text box 380 to illustrate the dimension of distance from a surface of the implant 310 to the endplate 348. Therefore, the user 220 may view the screen portion 370 to determine the dimension of the implant 310 relative to the endplate 348. Similarly, the user 220 can view the image portion 372 to determine the distance of a surface of the implant 310 relative to the endplate 350. Further, a text box 382 can illustrate the distance from the endplate 350.

The endplate images 348', 350' may be a single slice image or may include an average of several slices. As is known in the art, image data, such as in a CT image data, may be collected as a plurality of slices. The slices may each be a selected thickness, such as about 1 mm. To provide a general view of the boney portion which may include more than a small thickness (e.g. 1 mm) into the boney portion, several slices may be averaged together. For example, as illustrated in FIG. 2, a distance 361 may extend between planes that define or form the intervertebral area 360. A distance 345 into the vertebral body 344 may include about 2 mm to about 10 mm, and further include about 5 mm to about 10 mm. In various examples, the distance 345 may be about 10 mm. Thus, all slices within the distance 345 may be averaged together. The averaged image may then be displayed at the endplate 348'. Similarly, a distance 347 into the vertebral body 346 may include about 2 mm to about 10 mm, and further include about 5 mm to about 10 mm. In various examples, the distance 347 may be about 10 mm. Thus, all slices within the distance 347 may be averaged together. The averaged image may then be displayed at the endplate 350'.

The averaging of the slices to form the images 348', 350' may be formed with pixel averaging. For example, CT image slices are generally acquired along an axis, such as an axis of a spine including the vertebral bodies 344, 346. Thus, pixels from one slice to another may be aligned along the axis. The aligned pixels from several slices may be averaged together. In this way, one image may be generated that is based on averaging of several slices. It is understood that other appropriate averaging techniques may also be used.

The averaging allows the surgeon 220 to view portions, such as anatomical portions, that are not immediately adjacent the intervertebral space 360. For example, an anatomical feature (e.g. an osteophyte) may be 8 mm from the space 360. Thus, an image slice that is 1 mm or 2 mm thick would not image the osteophyte. However, in averaging a distance, such as about 10 mm, the osteophyte would be viewable in the averaged image that is displayed for the user 220. This may assist the user in selecting an appropriate implant and placing the selected implant.

The screen portion 374 may show image data that is substantially bounded by the implant dimensions. Thus, the screen portion 374 may not show any of the high contrast image data that is beyond the disc space 360. The screen portion 370 may show the endplate 348 that is away from the implant 310 in a superior direction. The screen portion 372 may show the endplate that is a distance away from the implant 310 in an inferior direction. Thus, the screen portions 370-374, together, may show image data that is limited to the planes or extent of the implant 310 (e.g. screen portion 374) along with image data that is spaced away from the implant 310 (i.e. screen portions 370 and 372). All of the screen portions, however, may be understood to be viewed along an axis of the spine 150 of the patient 152, but in the specific direction for the specific anatomical portion being viewed. Such direction information may also be provided on the screen portions regarding direction of view.

Accordingly, the display 256 including the screen portions 370-374 can be used by the user 220 to determine dimensions of the implant 310 relative to the anatomy, including the spine 150. Further, the display may change depending upon the implant or trial portion moved relative to the spine 150. For example, the user 220 can view the display 256 and, based upon the display, determine that the implant 310 is not appropriate for the subject 152. The user 220 may, then, attach a second or different trial portion to the instrument 300 and track it relative to the spine 150. The alternative trial may then be displayed on the display 256 relative to the various anatomy images 348', 350' to make the determination of whether the alternative or different trial portion is appropriate for the subject 152. Accordingly, it is understood that at least the dimensions of the icon illustrated in the implant 310' may be based upon dimensions of the specific implant portion being navigated by the user 220 that is attached to the instrument 300. The specific dimensions and/or shape of the implant 310 may be input into the navigation system 202 either manually by the user 220, based upon instructions of the user 220, or automatically based upon a communication between the trial implant portion 310 and the new navigation system 220. For example, a radio frequency identity tag (RFID tag) may be provided with the trial implant 310 that can communicate with the navigation system 202, including directly with the instrument 300, to provide selected dimension and shape information.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for displaying information, comprising:
a navigation system having a tracking system configured to determine a location of an instrument relative to at least a first portion of a subject and a second portion of the subject;
a display device configured to simultaneously display a first image of the first portion of the subject and a second image of the second portion of the subject; and
a navigation processor configured to execute instructions to determine the location of the instrument for illustrating with the display device a representation of the instrument in both a first direction relative to the first image of the subject and a second direction relative to the second image of the subject;
wherein the first image and the second image are images of portions a distance away from the instrument;
wherein the first direction is opposite to the second direction.

2. The system of claim 1, wherein the display device displays simultaneously both the first direction and the second direction along an axis relative to both the first image and the second image.

3. The system of claim 2, wherein the first image of the subject is an inferior endplate of a first vertebrae and the second image of the subject is a superior endplate of a second vertebrae, and the first direction of the first image is opposite the second direction of the second image.

4. The system of claim 3, wherein the display device is configured to display simultaneously both the representation of the instrument in the first direction relative to the first image and the representation in the second direction of the instrument relative to the second image.

5. The system of claim 4, wherein the navigation processor is further configured to determine a first distance of the instrument from at least one of the inferior endplate of the first vertebrae or a second distance of the instrument from the superior endplate of the second vertebrae;
wherein the display is configured to display at least one of a first distance amount or the second distance amount.

6. The system of claim 4, wherein the navigation processor is configured to scale the displayed representation of the instrument relative to either of the first image or the second image.

7. The system of claim 1, wherein the instrument includes a trial.

8. A system for displaying information, comprising:
a tracking system configured to determine a location of an instrument;
a display device configured to simultaneously display a first image portion of a subject and a second image portion of the subject including an icon representing a tracked location of the instrument; and
a processor configured to execute instructions to determine the location of the instrument for illustrating with the display device a representation of the instrument in at least one of a first perspective of the instrument relative to the first image portion of the subject and a second perspective of the instrument relative to the second image portion of the subject;
wherein the first perspective is opposite the second perspective.

9. The system of claim 8, wherein the processor is further configured to automatically determine the first perspective of the instrument relative to the first image portion of the subject and the second perspective of the instrument relative to the second image portion of the subject and the display device is configured to display the first perspective and the second perspective.

10. The system of claim 8, wherein the first image portion incudes a first vertebral endplate and the second image portion includes a second endplate;

wherein the processor is further configured to determine the first perspective of the instrument relative to the first endplate and the second perspective of the instrument relative to the second endplate.

11. The system of claim 10, wherein the display device is configured to display both the first perspective and the first endplate and the second perspective and the second endplate.

12. The system of claim 11, further comprising:
the instrument configured to move a trial member relative to the subject;
a tracking device associated with the instrument configured to be tracked with the tracking system.

13. A method of displaying information for a user, comprising:
determining a location of an instrument relative to a portion of a subject;
displaying with a display device a first image based on image data acquired of the subject including a low contrast portion of the subject;
displaying with the display device a second image based on image data acquired of the subject including a first high contrast portion of the subject;
displaying with the display device a third image based on image data acquired of the subject including a first high contrast portion of the subject;
subject including a second high contrast portion of the subject;
superimposing a first icon representing the instrument on the displayed first image;
superimposing a second icon representing the instrument on the displayed second image;
superimposing a third icon representing the instrument on the displayed third image;
wherein the second image is taken from a first direction and the third image is taken from a second direction, where the first direction is opposite the second direction.

14. The method of claim 13, further comprising:
acquiring image data of the subject, wherein the subject includes tissue that has low contrast in the image data.

15. The method of claim 13, further comprising:
simultaneously displaying with the display device the first image and the first icon superimposed on the first image and displaying with the display device the second image and the second icon superimposed on the second image.

16. The method of claim 13, wherein the second image is a first endplate and the third image is a second endplate;
wherein the first endplate and the second endplate form an intervertebral space.

17. The method of claim 13, further comprising:
updating the second icon superimposed on the second image based on a movement of the instrument.

* * * * *

UNITED STATES PATENT AND TRADEMARK OFFICE
CERTIFICATE OF CORRECTION

| | |
|---|---|
| PATENT NO. | : 11,819,290 B2 |
| APPLICATION NO. | : 17/096164 |
| DATED | : November 21, 2023 |
| INVENTOR(S) | : Alan J. Schnarr et al. |

It is certified that error appears in the above-identified patent and that said Letters Patent is hereby corrected as shown below:

On the Title Page

Column 1, item (72) Inventors, Line 5, After "L", insert --.--

In the Specification

Column 6, Detailed Description, Line 11, Delete "330 271" and insert --330, 271-- therefor Column 7, Detailed Description, Line 60, Delete "152" and insert --150-- therefor Column 9, Detailed Description, Line 10, Delete "disk" and insert --disc-- therefor Column 9, Detailed Description, Line 13, Delete "disk" and insert --disc-- therefor Column 11, Detailed Description, Line 32, Delete "220." and insert --202.-- therefor In the Claims Column 12, Line 66, In Claim 10, Delete "incudes" and insert --includes-- therefor Signed and Sealed this
Twelfth Day of November, 2024

Katherine Kelly Vidal
*Director of the United States Patent and Trademark Office*